(12) United States Patent
Hamilton et al.

(10) Patent No.: US 10,172,700 B2
(45) Date of Patent: Jan. 8, 2019

(54) PROSTHESIS FOR REPAIRING A HERNIA DEFECT

(71) Applicant: C.R. Bard Inc., Murray Hill, NJ (US)

(72) Inventors: Jason Hamilton, Dartmouth, MA (US); Augustus Felix, Cranston, RI (US); Elizabeth Blackburn, Cranston, RI (US); Kerri MacDonald, Franklin, MA (US)

(73) Assignee: C.R. Bard, Inc., Murray Hill, NJ (US)

( * ) Notice: Subject to any disclaimer, the term of this patent is extended or adjusted under 35 U.S.C. 154(b) by 720 days.

(21) Appl. No.: 14/556,297

(22) Filed: Dec. 1, 2014

(65) Prior Publication Data

US 2016/0151136 A1    Jun. 2, 2016

(51) Int. Cl.
*A61F 2/02* (2006.01)
*A61F 2/00* (2006.01)

(52) U.S. Cl.
CPC .......... *A61F 2/0063* (2013.01); *A61F 2/0077* (2013.01); *A61F 2002/0068* (2013.01); *A61F 2002/0072* (2013.01)

(58) Field of Classification Search
CPC .................. A61F 2/0063; A61F 2002/0072
See application file for complete search history.

(56) References Cited

U.S. PATENT DOCUMENTS

| 460,940 | A | 10/1891 | Baugh |
|---|---|---|---|
| 5,116,357 | A | 5/1992 | Eberbach |
| 5,141,515 | A | 8/1992 | Eberbach |
| 5,147,374 | A | 9/1992 | Fernandez |
| 5,176,692 | A | 1/1993 | Wilk et al. |
| 5,258,000 | A | 11/1993 | Gianturco |
| 5,333,624 | A | 8/1994 | Tovey |
| 5,366,460 | A | 11/1994 | Eberbach |
| 5,368,602 | A | 11/1994 | de la Torre |
| 5,370,650 | A | 12/1994 | Tovey et al. |
| 5,395,383 | A | 3/1995 | Adams et al. |

(Continued)

FOREIGN PATENT DOCUMENTS

| EP | 0557964 A1 | 1/1993 |
|---|---|---|
| EP | 1336391 | 8/2003 |

(Continued)

OTHER PUBLICATIONS

International Search Report and Written Opinion for International Application No. PCT/US2015/062960, dated Mar. 8, 2016, 13 pages.

(Continued)

*Primary Examiner* — Sarah W Aleman
(74) *Attorney, Agent, or Firm* — Wolf, Greenfield & Sacks, P.C.

(57) ABSTRACT

A prosthesis for repairing a hernia defect includes a patch body, a hoisting frame releasably attachable to the patch body, and a tether attached to the hoisting frame and having a free end extendable through the thickness of the patch body and accessible from the side of the patch body opposite to the side where the hoisting frame is releasably attached. The patch body and/or the hoisting frame includes a self-expanding support member. The hoisting frame includes a frame body and a translation component for directing pulling forces on the tether to the frame body.

23 Claims, 2 Drawing Sheets

(56) References Cited

U.S. PATENT DOCUMENTS

| | | |
|---|---|---|
| 5,397,332 A | 3/1995 | Kammerer et al. |
| 5,405,360 A | 4/1995 | Tovey |
| 5,634,931 A | 6/1997 | Kugel |
| 5,797,960 A | 8/1998 | Stevens et al. |
| 5,824,082 A | 10/1998 | Brown |
| 5,916,225 A | 6/1999 | Kugel |
| 5,919,232 A | 7/1999 | Chaffringeon et al. |
| 5,957,939 A | 9/1999 | Heaven et al. |
| 6,258,113 B1 | 6/2001 | Adams et al. |
| 6,391,060 B1 | 5/2002 | Ory et al. |
| 6,565,590 B2 | 5/2003 | Kieturakis et al. |
| 6,575,988 B2 | 6/2003 | Rousseau |
| 6,616,685 B2 | 9/2003 | Rousseau |
| 6,702,827 B1 | 3/2004 | Lund et al. |
| 6,911,037 B2 | 6/2005 | Gainor et al. |
| 7,235,042 B2 | 6/2007 | Vanden Hoek et al. |
| 7,273,489 B2 | 9/2007 | Boudjemline |
| 7,377,936 B2 | 5/2008 | Gainor et al. |
| 7,824,420 B2 | 11/2010 | Eldridge et al. |
| 7,947,054 B2 | 5/2011 | Eldar et al. |
| 8,388,633 B2 | 3/2013 | Rousseau et al. |
| 8,500,762 B2 | 8/2013 | Sholev et al. |
| 8,562,633 B2 | 10/2013 | Cully et al. |
| 9,439,643 B2 | 9/2016 | Darois et al. |
| 9,504,548 B2 | 11/2016 | Darois et al. |
| 9,642,689 B2 | 5/2017 | Sholev et al. |
| 10,034,736 B2 | 7/2018 | Blackburn et al. |
| 2002/0103494 A1 | 8/2002 | Pacey |
| 2002/0133236 A1 | 9/2002 | Rousseau |
| 2004/0019360 A1 | 1/2004 | Farnsworth et al. |
| 2004/0087980 A1 | 5/2004 | Ford et al. |
| 2005/0049635 A1 | 3/2005 | Leiboff |
| 2005/0171569 A1 | 8/2005 | Girard et al. |
| 2006/0015143 A1 | 1/2006 | Alvarado |
| 2006/0247586 A1 | 11/2006 | Voegele et al. |
| 2007/0066980 A1 | 3/2007 | Leahy |
| 2007/0185506 A1 | 8/2007 | Jackson |
| 2007/0260179 A1 | 11/2007 | Sholev et al. |
| 2007/0265710 A1 | 11/2007 | Brown et al. |
| 2008/0065229 A1 | 3/2008 | Adams |
| 2008/0195121 A1 | 8/2008 | Eldar et al. |
| 2009/0254103 A1 | 10/2009 | Deutsch |
| 2009/0270999 A1 | 10/2009 | Brown |
| 2010/0069947 A1 | 3/2010 | Sholev et al. |
| 2010/0241145 A1 | 9/2010 | Cook |
| 2010/0261953 A1 | 10/2010 | Townsend et al. |
| 2010/0261954 A1 | 10/2010 | Townsend et al. |
| 2010/0261956 A1 | 10/2010 | Townsend et al. |
| 2010/0292718 A1 | 11/2010 | Sholev et al. |
| 2011/0011407 A1 | 1/2011 | Townsend et al. |
| 2011/0054500 A1 | 3/2011 | Levin et al. |
| 2011/0112560 A1 | 5/2011 | Sholev |
| 2011/0118706 A1 | 5/2011 | Gingras et al. |
| 2011/0152897 A1 | 6/2011 | Bates |
| 2011/0224704 A1 | 9/2011 | Bailly et al. |
| 2011/0288567 A1* | 11/2011 | Ranucci ............... A61F 2/0063 606/151 |
| 2011/0295283 A1 | 12/2011 | Darois et al. |
| 2012/0065649 A1 | 3/2012 | Towler |
| 2013/0035704 A1 | 2/2013 | Dudai |
| 2013/0060263 A1 | 3/2013 | Bailly et al. |
| 2013/0103042 A1 | 4/2013 | Davis |
| 2013/0103058 A1 | 4/2013 | Gobran |
| 2013/0178876 A1 | 7/2013 | Horton et al. |
| 2013/0218178 A1 | 8/2013 | Shandas |
| 2013/0218179 A1 | 8/2013 | Sholev et al. |
| 2013/0231526 A1 | 9/2013 | Felix et al. |
| 2013/0267970 A1 | 10/2013 | Cardinale et al. |
| 2014/0025093 A1 | 1/2014 | Horton et al. |
| 2014/0051915 A1 | 2/2014 | Sholev et al. |
| 2014/0058416 A1 | 2/2014 | Brown |
| 2014/0088343 A1 | 3/2014 | Arcand et al. |
| 2014/0088619 A1* | 3/2014 | Cardinale ........... A61B 17/0057 606/151 |
| 2014/0188250 A1 | 7/2014 | Fearnot et al. |
| 2015/0148824 A1 | 5/2015 | Horton et al. |
| 2015/0157437 A1 | 6/2015 | Cohen et al. |
| 2015/0209129 A1 | 7/2015 | Bailly et al. |
| 2015/0250576 A1 | 9/2015 | Blackburn et al. |
| 2015/0257866 A1* | 9/2015 | Filipiak ................. A61F 2/0063 606/151 |
| 2017/0100229 A1 | 4/2017 | Darois et al. |
| 2017/0181831 A1 | 6/2017 | Felix et al. |
| 2017/0181832 A1 | 6/2017 | Felix et al. |
| 2017/0181833 A1 | 6/2017 | Felix et al. |

FOREIGN PATENT DOCUMENTS

| | | |
|---|---|---|
| EP | 1971275 | 8/2007 |
| FR | 2769825 A1 | 4/1999 |
| WO | WO 13/007535 | 1/2003 |
| WO | WO 2003/002029 | 1/2003 |
| WO | WO 2007/087146 A2 | 8/2007 |
| WO | WO 2007/087146 A3 | 8/2007 |
| WO | WO 2007/115110 A2 | 10/2007 |
| WO | WO 2010/027898 | 3/2010 |
| WO | WO 2010/039249 | 4/2010 |
| WO | WO 2010/059234 | 5/2010 |
| WO | WO 2011/137224 A1 | 11/2011 |
| WO | WO 2012/047414 A1 | 4/2012 |
| WO | WO 2013/007534 A1 | 1/2013 |
| WO | WO 13/048272 | 4/2013 |
| WO | WO 2013/049791 A1 | 4/2013 |
| WO | WO 2013/049795 A1 | 4/2013 |
| WO | WO 2013/062933 A1 | 5/2013 |
| WO | WO 2013/142353 A1 | 9/2013 |
| WO | WO 2013/148719 | 10/2013 |
| WO | WO 2013/148839 A1 | 10/2013 |

OTHER PUBLICATIONS

International Preliminary Report on Patentability for International Application No. PCT/US2015/062960, dated Jun. 15, 2017, 8 pages.
U.S. Appl. No. 14/636,514, filed Mar. 3, 2015, Blackburn et al.
U.S. Appl. No. 15/389,943, filed Dec. 23, 2016, Felix et al.
U.S. Appl. No. 15/389,948, filed Dec. 23, 2016, Felix et al.
U.S. Appl. No. 15/389,957, filed Dec. 23, 2016, Felix et al.
U.S. Appl. No. 16/030,091, filed Jul. 9, 2018, Blackburn et al.

* cited by examiner

PROSTHESIS FOR REPAIRING A HERNIA DEFECT

FIELD

A prosthesis for repairing a hernia defect.

BACKGROUND

A hernia defect is an opening or weakness in a tissue or muscle wall, such as the abdominal wall. One approach for repairing a hernia is to cover the tissue or muscle wall defect with a patch of repair fabric. The patch may be placed in an open procedure or through a minimally invasive procedure, such as by a laparoscopic technique. In a laparoscopic hernia repair, a patch is delivered through a narrow cannula to a treatment site within the patient. As the patch is much larger than the cannula bore, the patch must be reduced in size to enable passage through the small opening into the patient. After laparoscopic deployment, the patch needs to return to an enlarged shape sufficient to cover the defect. Certain hernia repair patches include a resilient support member, such as an elastic wire, that is collapsed along with the patch into a reduced configuration and delivered through the laparoscopic cannula. After exiting the cannula, the resilient support member unfurls causing the associated patch to expand into the enlarged repair configuration. The expanded patch including the resilient support member is then fixated to the tissue or muscle wall over the defect.

SUMMARY

According to one aspect, a prosthesis for repairing a hernia defect includes a patch body having a periphery, a first axis and a second axis perpendicular to the first axis, the first axis and the second axis intersecting at approximately a center of the patch body. An upper portion of the patch body is on one side of the first axis and a lower portion of the patch body on the other side of the first axis. A self-expanding support member assists in unfurling the patch body from the reduced configuration to an expanded configuration, the self-expanding support member including a first portion that is positionable on the upper portion of the patch body and a second portion that is positionable on a lower portion of the patch body. A hoisting frame is releasably attachable to the patch body, the hoisting frame defining an open interior and including a translation component extending through the open interior. A tether is attached to the translation component. A free end of the tether is extendable away from the translation component and through the patch body when the hoisting frame is releasably attached to the patch body. A pulling force on the free end of the tether in an outward direction away from the patch body is directed by the translation component in the direction of a first pair of spaced apart locations on opposite sides of the second axis at the upper portion of the patch body when in the expanded configuration and a second pair of spaced apart locations on opposite sides of the second axis at the lower portion of the patch body. The patch body and the hoisting frame, when releasably attached to the patch body, are manipulable into a reduced configuration for insertion through a narrow incision or cannula into a patient.

According to another aspect, a prosthesis for repairing a hernia defect includes a patch body having a periphery, a first axis and a second axis perpendicular to the first axis, the first axis and the second axis intersecting at approximately a center of the patch body. An upper portion of the patch body is on one side of the first axis and a lower portion of the patch body on the other side of the first axis. A hoisting frame defines an open interior and is releasably attachable to the patch body. The hoisting frame including a self-expanding support member to assist in unfurling the patch body from the reduced configuration into an expanded configuration when the frame is releasably attached to the patch body. The hoisting frame has a first axis and a second axis perpendicular to the first axis, the first axis and the second axis intersecting at approximately a center of the hoisting frame. The hoisting frame has an upper portion on one side of the hoisting frame first axis and a lower portion on an opposite side of the hoisting frame first axis. The hoisting frame further includes at least two non-self-expanding arms at spaced locations in the open interior on opposite sides of the second axis of the hoisting frame at the both the upper and the lower portions of the hoisting frame. The non-self-expanding arms including a tether attachment portion. A tether is connected to the tether attachment portion and includes a free end that is extendable away from the hoisting frame and through the patch body when the hoisting frame is releasably attached to the patch body. A pulling force on the free end of the tether in an outward direction away from the hoisting frame is directed by the first and second arms to the spaced apart locations on opposite sides of the second axis of the hoisting frame at both the upper and lower portions of the hoisting frame. The patch body and the hoisting frame, when releasably attached to the patch body, are manipulable into a reduced configuration for insertion through a narrow incision or cannula into a patient.

According to another aspect, a prosthesis for repairing a hernia defect includes a patch body having a periphery, a first axis and a second axis perpendicular to the first axis, the first axis and the second axis intersecting at approximately a center of the patch body. A hoisting frame is releasably attachable to the patch body. The hoisting frame has a frame body defining an open interior and includes a first axis and a second axis perpendicular to the first axis. The first axis and the second axis intersect at approximately a center of the frame body which is registrable with the center of the patch body when the hoisting frame is releasably attached to the patch body. The frame body includes an upper portion on one side of the first axis and a lower portion on an opposite side of the first axis. The hoisting frame further includes a first pair of attachment locations at the upper portion and on opposite sides of the second axis for releasably attaching the hoisting frame to the patch body, and a second pair of attachment locations at the lower portion and on opposite sides of the second axis for releasably attaching the hoisting frame to the patch body. The hoisting frame further includes a force translation component extending from the first and second pair of attachment locations and through or adjacent the approximate center. A tether is attached to a portion of the force translation component extending through or adjacent the approximate center. The patch body and the hoisting frame, when releasably attached to the patch body, are manipulable into a reduced configuration for insertion through a narrow incision or cannula into a patient.

BRIEF DESCRIPTION OF DRAWINGS

Aspects of the invention are described below with reference to the following drawings in which like numerals reference like elements, and wherein.

DETAILED DESCRIPTION

It should be understood that aspects of the invention are described herein with reference to certain illustrative embodiments and the figures. The illustrative embodiments described herein are not necessarily intended to show all aspects of the invention, but rather are used to describe a few illustrative embodiments. Thus, aspects of the invention are not intended to be construed narrowly in view of the illustrative embodiments. In addition, it should be understood that aspects of the invention may be used alone or in any suitable combination with other aspects of the invention.

Various embodiments are described in connection with the repair of a hernia, specifically a ventral hernia. However, the invention is not necessarily so limited, and may be employed to repair other types of hernias, other soft tissue or muscle wall defects, as well as may be used in other surgical or medical treatments. With respect to repair of a ventral hernia, the repair patch may be placed in the intraperitoneal, preperitoneal, retromuscular, or other anatomical space, as the invention is not so limited. For ease of understanding, the hernia repair patch is described in connection with a laparoscopic procedure but may be employed in other minimally invasive procedures, in an open procedure, or in other techniques for repairing a hernia or other soft tissue defect as should be apparent to one of skill in the art.

A patch for repairing a hernia may include a patch body having a first side that will be positioned against a tissue or muscle wall, such as the abdominal wall, that includes the defect. The first side of the patch body may be configured for tissue ingrowth. Where the patch will be located adjacent sensitive organs, such as the intestines or other viscera, an opposite side of the patch body may include a barrier, such as a layer of barrier material or a barrier coating, to prevent adhesions between the first side of the patch and the sensitive organs.

In a minimally invasive technique, as well as in certain open procedures, a hernia repair patch may be reduced in size to facilitate delivery of the prosthetic device to the treatment site. For example, in a laparoscopic procedure, a hernia repair patch may be rolled into a slender cylindrical shape, or otherwise collapsed into a smaller configuration, suitable for passage through a narrow cannula which may have an inner diameter of approximately 10 mm, of approximately 5 mm, or even a finer size. After delivery to the surgical site, the reduced hernia repair patch is transformed into an expanded configuration. The enlarged patch is then placed against the abdominal wall and may be fixated by sutures, staples, tacks and/or other fixation elements. For example, such fixation elements may be applied through a border region, and/or at other locations, of the patch into healthy tissue surrounding the defect.

A hoisting frame may be employed to provisionally hold the expanded patch against the abdominal wall pending fixation. The frame may include a frame body and fixating component at various locations on the frame body to releasably attach the hoisting frame to the patch. Such locations may be in the form of lands, other portions of the frame body, and other regions of the frame body as should be apparent to one of skill in the art. The hoisting frame may be compliant to facilitate its collapsibility when the assembled patch and hoisting frame are rolled up or otherwise reduced in shape for minimally invasive delivery. A tether extends from the hoisting frame and is passed through the patch body so that its free end is accessible on the side of the patch body opposite to the hoisting frame. When the assembled patch and frame have unfurled to an expanded shape at the surgical site, the tether may be drawn through the abdominal wall to outside of the patient. Continued pulling of the tether will draw the frame, and patch body supported by the frame, upwardly against the abdominal wall.

The frame may include a translation component configured so that a pulling force on the tether in an outward direction away from the frame and the patch body is directed by the translation component in different directions relative to an axis extending through an approximate center of the frame towards both the upper and the lower portions of the frame. Such a translation of the pulling force in different direction towards both the upper and lower portions of the frame assists in spreading the hoisting force about the frame. The direction of the translated forces may range from 70 degrees to 5 degrees on each side of the second axis. For example, and without limitation, the direction of the translated forces may be +/−30 degrees, +/−45 degrees, or such other combination of differing force angles relative to the second axis. As should be apparent to one of skill in the art, the direction of forces by the translation component on one side of the axis need not mirror the direction of forces on the other side of the axis, nor need the forces translated towards the upper portion have the same direction as the forces transmitted towards the lower portion. For example, and without limitation, the translation component could be configured to direct forces at +/−30° relative to the second axis at the upper portion and +/−45° relative to the second axis at the bottom portion. Further, in certain embodiments, the translation component may transmit the forces in the direction of the locations of fixating component of the hoisting frame to the patch body.

The translation component may include a pair of arms each of which direct forces to locations on opposites sides of the second axis. The pair of arms may be arranged in an X-shape. Other patterns of translation arms are contemplated; for example, the arms may have an H-shape or other configuration as should be apparent to one of skill in the art. The translation component may be configured so as not to be self-expanding. That is, the translation component may be compliant but not notably resilient nor possessing shape memory.

To assist in unfurling the patch into an expanded shape after minimally invasive deployment, a support member may be associated with the hoisting frame and/or the patch body. The support member may have a resiliency or other property (e.g., shape memory) that allows the support member to deform from an initial, expanded, shape into a compact configuration as the patch is reduced in size for laparoscopic or other minimally invasive delivery, and then return to the initial shape, or at least to a shape larger than the reduced shape, upon reaching the delivery site. Such an ability to revert from a collapsed configuration to an expanded configuration without requiring assistance of a medical professional is referred to herein as a "self-expanding" support member. Recovery of the support member causes the patch to spread out into an expanded configuration. For example, and without limitation, the support member may be rollable into a reduced size for delivery to the hernia repair site. A representative support member may be formed from a nitinol wire. The support member may have a frame-like shape and may generally follow the periphery of the patch. Representative shapes of a support member include circular, oval or a polygon. The support member may be contained within the hoisting frame, attached to the surface of the hoisting frame, woven in undulating fashion through the hoisting frame, or otherwise associated with the hoisting frame. It also is contemplated to form the hoisting frame with self-expanding properties. In addition, or alternatively, a self-expanding frame may be provided with the patch body.

The frame may have a thin profile to provide a reduced configuration when collapsed with the patch body for minimally invasive delivery. The frame may be in the form of a flat sleeve (e.g., sheath), for example from opposed thin pieces of fabric such as NYLON that are fused or otherwise joined together, at least in those portions of the frame where a self-expanding support member will be contained therein. The translation component extending between opposite edges of the frame may be formed of the same material that constitutes the frame or of a different material. In either case, the translation component also may present a thin profile to provide a slender shape when the frame and patch body are rolled up or otherwise collapsed for minimally invasive delivery. The tether may be in the form of a suture, a strap such as a strip of mesh fabric, a combination suture and strap, or constructed from other or additional components as should be apparent to one of skill in the art. The tether may be tied to, bonded or fused with, or otherwise attached by any appropriate method with, the translation component. Alternatively, the translation component and the tether may be integrally formed together as a unitary structure. In certain embodiments, the translation component extends to various fixating components for releasably connecting the hoisting frame to the patch body.

The hoisting frame, and the support member when located remote from the hoisting frame, may be characterized by their positioning relative to the axes of the patch body. For example, the frame and the support member where disassociated from the frame, may include a first portion that is positionable on an upper portion of the patch body relative to the first axis, and a second portion that is positionable on an opposite, lower portion of the patch body relative to the first axis. Each of the first portion and the second portion may have a curved profile, although straight, compound straight, angled and/or curved, and other profiles are contemplated as should be apparent to one of skill in the art. The hoisting frame, and the support member when not associated with the hoisting frame, may include lateral and medial portions which may have similar or different profiles as compared to the top and bottom portions.

With the patch body spread out over the hernia defect, and secured to the tissue or muscle wall, the inventors have recognized that there no longer is need for the hoisting frame and associated support member. Accordingly, the hoisting frame, as observed earlier, may be releasably attached to the hernia repair patch, allowing selective removal of the hoisting frame and associated support member by the surgical team after expanding, positioning, and/or fixation of the patch body. Detachment of the frame will, in turn, separate the support member if associated with the frame, from the fixated patch body. The detached frame and associated support member may then be removed from the patient, such as by withdrawal through the same narrow opening in which the patch and hoisting frame had been delivered minimally invasively into the patient.

In one embodiment, the releasable fixating components for connecting the frame to the patch body include a coil-type fixating component that are provided at various locations, such as at a land or projection, about the frame body. The coil-type fixating component may have an extended, linear configuration that facilitates passing the fixating component into, and removing the fixating component from, the patch body and a retracted, coiled configuration which retains the patch body. Other arrangements for releasably attaching the frame to the patch body also are contemplated. For example, and without limitation, a suture may run between the frame, such as at a land, and the patch body. The suture can be cut at one or more locations and then the frame pulled away from the patch body. Alternatively, the suture may be sufficiently weak or be modified to include one or more localized weak points that will fail upon application of a sufficient pulling force. Alternatively, the frame, such as at a land, may be adhered by a relatively weak adhesive to the patch body. Another option is to configure the frame and/or patch body so as to releasably engage each other. In one such arrangement, the patch body may include one or more slits that releasably receive an aspect of the frame.

The frame body and patch body may have generally the same shape or different shapes. For example, the patch body could be rectangular and the frame body oval. In one embodiment, the hoisting frame includes a generally oval frame body that contains a generally oval self-expanding support member. A translation component, such as X-shaped arms, extends between top and bottom aspects of the oval portion of the hoisting frame. At or near the junction of the translation arms and the oval portion of the frame are fixating components for releasably attaching the hoisting frame to a patch body. The fixating components, such as coil fasteners, may be located on lands that extend interiorly and/or exteriorly of the oval portion of the frame.

As shown in FIGS. 1-5, a prosthesis for repairing a hernia or other soft tissue defect 10 may include a patch body 12 having a first surface 14 that is arranged for tissue ingrowth and a second surface 16 that is configured as a barrier to adhesions between the first surface and sensitive organs or tissue, such as the intestines or other viscera. The first surface may include a tissue infiltratable layer such as a mesh or other porous fabric amenable to tissue ingrowth, and the second surface may be a solid or substantially non-porous barrier layer or a barrier coating that will prevent contact between the viscera and the porous tissue ingrowth fabric. The patch body may be defined by a first axis 18 and a second axis 20 that is substantially perpendicular to the first axis. The intersection of the first and second axes may coincide with a center, or approximate center 22, of the patch body. Alternative arrangements of a patch body are contemplated as should be apparent to one of skill in the art. For example, and without limitation, the patch body may include only a tissue infiltratable layer, only a solid or non-tissue infiltratable layer, or a combination of tissue infiltratable and non-tissue infiltratable aspects situated in the same layer.

Figures 1, 4:
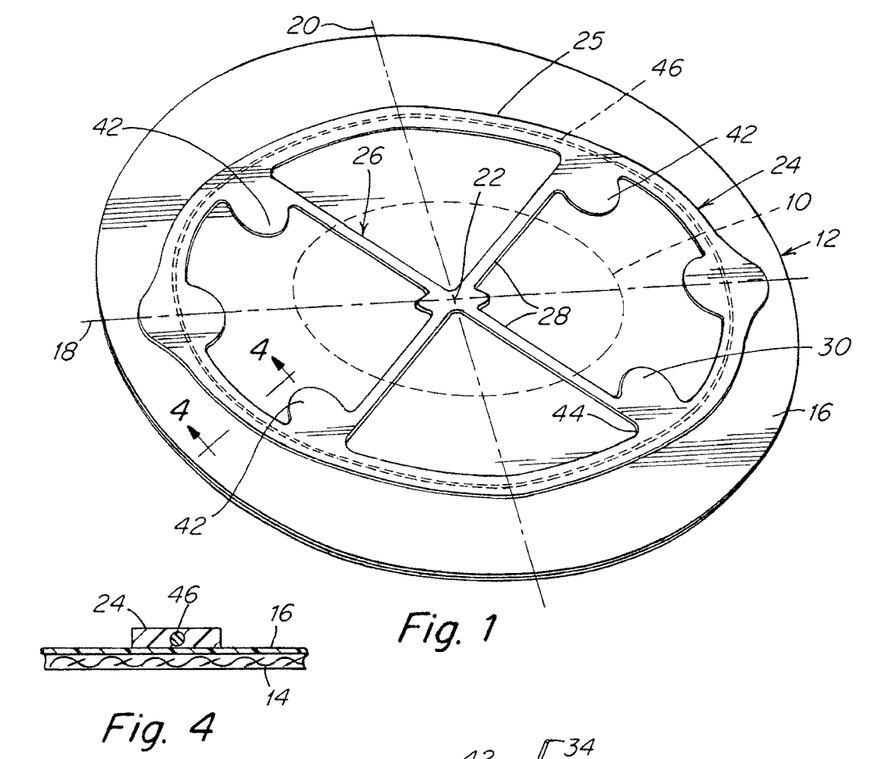
FIG. 1 is an illustration of a prosthesis for repairing a hernia defect with an assembled hernia repair patch and hoisting frame in an expanded configuration.
FIG. 4 is sectional illustration along line 4-4 of FIG. 1.
Figure 2:
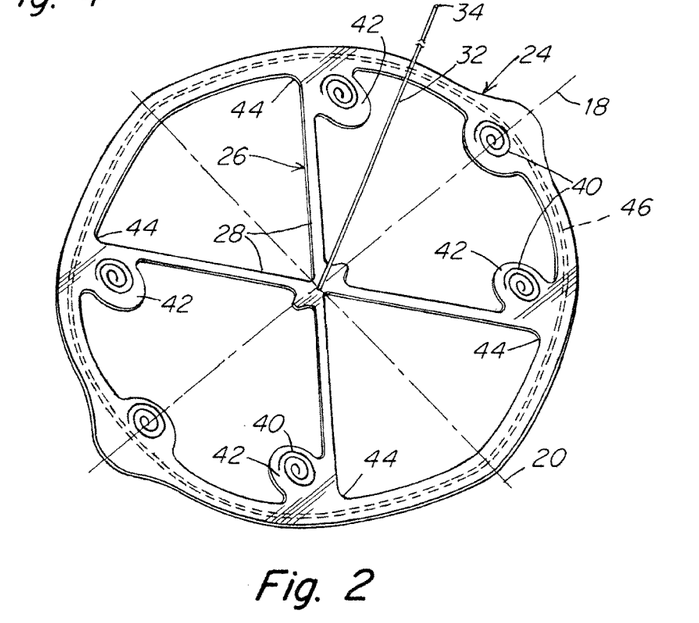
FIG. 2 is an illustration of a patch body side of a hoisting frame with a tether extending from the hoisting frame.
Figure 3:
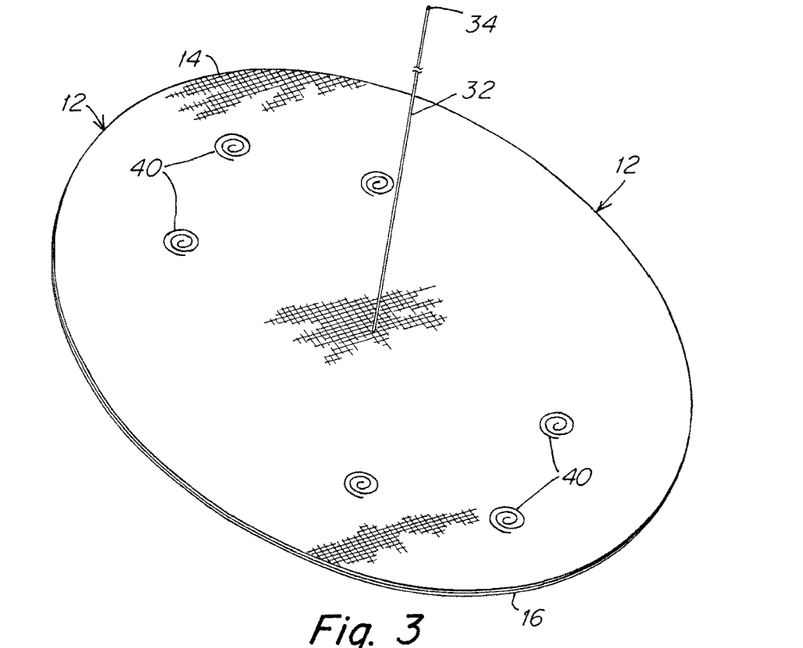
FIG. 3 is an illustration of an assembled patch body, frame and tether, with fixation components securing the patch body to the frame and the tether extending from the frame through the thickness of the patch body and being accessible on the side of the patch body opposite the frame body.

A hoisting frame 24 may be positioned adjacent the second surface and may extend generally around the periphery of the patch body as illustrated in FIG. 1. The frame may have a thin or reduced profile and may, for example and without limitation, be in the form of a flat sleeve or sheet so as to minimize the overall thickness of the patch when assembled with the frame and reduced for delivery through a narrow opening to the treatment site. The frame may be a continuous component or may include two or more discrete segments that are contiguous and/or spaced from each other which in combination form a frame body. The frame body 25 defines a generally open interior space through which fixation elements such as sutures, tacks, staples or other devices may be applied to secure the patch body to the abdominal wall. A force translating component 26 extends across the open frame body interior. The force translating component may be connected to the portion 30 of the frame supporting the fixating components that releasably attach the hoisting frame to the patch body and/or to other portions of the frame body. A portion of the force translating component extends through a central region of the frame. A tether 32 extends from the central region. A free end 34 of the tether is passed through the thickness of the patch body so that it extends beyond the side of the patch body opposite the hoisting frame.

During the procedure, the tether may be drawn through the abdominal wall to outside of the patient. A pulling force on the free end of the tether in an outward direction away from the hoisting frame and the patch body is directed by the translation component to the junction of the translation component and the fixating components and/or the frame body. The resultant translated forces spread the pulling force about the frame body, facilitating hoisting of the frame and associated patch body against the abdominal wall. The force translating component may have an angle $\ominus$ relative to the second axis. $\ominus$ may range from 70 degrees to 5 degrees on each side of the second axis. For example, and without limitation, the direction of the translated forces may be +/−30°, +/−45°, or such other combination of force direction relative to the second axis (where "+" is one side of the axis and "−" is the other side of the axis). The force translating component may include an X-shape, and H-shape, or other shape suitable to transmit the pulling force on the tether to outward and lateral aspects of the frame body and/or fixation components. The force translating component may be characterized by a pair of arms 28 that extend on opposite sides of the second axis, with a portion of the pair of arms extending through or near an approximate center of the frame body. Although the translation component is shown with arms that are symmetric about the first and second axes, they need not be so as should be apparent to one of skill in the art. That is, the translation component may be asymmetric about one or both of the first and second axes of the hoisting frame.

The frame may be releasably attached to the patch body via one or more fixating components 40. In one embodiment, the fixating component has an unretracted configuration, such as substantially straight, that is adapted to attach or detach the fixation component to the patch body, thus allowing connection or release of the patch body from the hoisting frame. The fixating component has a retracted configuration, such as substantially coiled, to retain the patch body to the fixation component and, in turn, the hoisting frame. One end of the fixating component may be connected to the frame, such as at a land 42. A free end of the fixating component may be sharpened or otherwise adapted to pierce through the patch body. Thus, in the unretracted configuration the free end of the fixating component may be passed through the patch body and will remain passed through the patch body to retain the patch to the frame when in the retracted configuration. The fixating components may be located anywhere along the frame including at land portions 42 of the frame. The fixating components may be positioned at or near portions of the translation component including, but not limited to, at or near portions of the junction 44 of the translation component and the frame body. Fixation components may additionally, or alternatively, be located along either axis of the patch frame. As illustrated, fixation components may be positioned at lands along the first axis at opposite sides of the frame body. In certain embodiments, the frame body, the lands, and the translating component, lie in the same plane and present a thin, planar profile when the frame body is in an expanded configuration.

Figure 5:
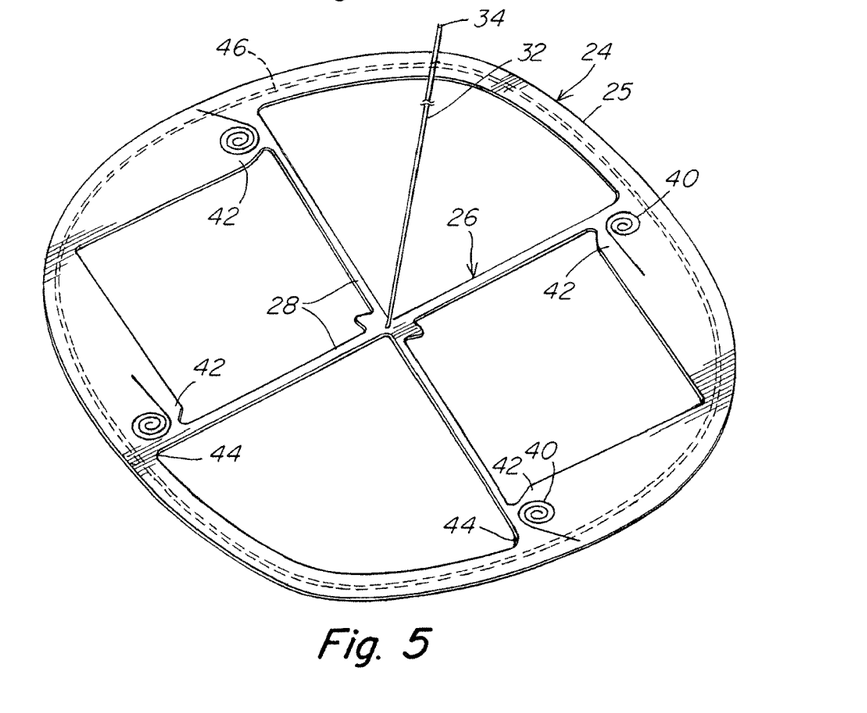
FIG. 5 an illustration of a patch body side of an alternative hoisting frame with a tether extending from the hoisting frame.

The peripheral portion of the frame body may be enlarged at various locations to enhance support of the hernia repair patch when the patch and frame body have been unfurled. FIG. 5, for example, shows bulked segments of a frame body at opposite ends of the frame and about a first axis as compared to the frame body illustrated in FIG. 2. The enlarged segments may include the land portions at which the fixation components are positioned.

Contained within the frame body may be a self-expanding support member 46, such as an elastic wire, that will assist in unfurling the patch body into an expanded shape after laparoscopic delivery to the treatment site. The support member may be formed of nitinol, other super-elastic metals, appropriately resilient metals, plastics or other materials, other shape memory metals or plastics, and comparable materials as should be apparent to one of skill in the art. The self-expanding support member may be continuous or formed of two or more spaced segments. The self-expanding support member may have any appropriate shape for transforming the patch body into a desired expanded shape. Representative shapes include, but are not limited to, circular, oval or a polygon.

In some embodiments, the frame body may be in the form of a thin, flat textile structure having a bottom surface and a top surface, and at least one of the top and bottom surfaces may have a substantially flat shape. In one embodiment, the bottom surface that faces the patch body may have a flat shape, with the top surface having a curved profile. In other embodiments, a wall may be located between the long edges of the top and bottom surfaces. The top and bottom surfaces may be separated only where the support member is sandwiched therebetween. The frame body, then, is solid. The frame may be formed of a NYLON material, other synthetic polymers, as well as natural materials. The translating component also may be formed of a thin, flat textile structure and may be composed of the same or of different material as the frame body. The translating component may be in the form of a strip, sheath, or spoke, for example, or other suitable force translating configuration as should be apparent to one of skill in the art. In certain embodiments, the translating component and the frame may be integrally formed as a unitary structure.

Various techniques may be employed to reduce the assembled patch and frame to a smaller configuration suitable for delivery through a narrow opening, such as via a laparoscopic cannula. For example, and without limitation, the assembled patch and frame, may be rolled up into a cylinder. In one embodiment, an introducer includes a shaft having a patch receiving area that may be defined, for example, between splined sections of the shaft. The patch receiving area may threadably receive the patch. Rotating the shaft will cause the patch to roll up about the shaft in the area of the patch receiving area.

The patch body may have any form appropriate for repairing a hernia defect. The patch may be substantially flat or may be arranged with a concave, convex, or a combination concave/convex surface. The distance between edges of the patch body along the first axis may be greater than the distance between edges of the patch body along the second axis; that is, the patch body may be elongated along the first axis. The shape of the patch body when viewed along the first axis may be different than the shape of the patch body when viewed along the second axis. For example, and without limitation, the edges of the patch body intersected by the first axis may be generally round while the edges of the patch body intersected by the second axis may be linear and run parallel to the first axis. Without wishing to be bound by any theory, the linear edges provide a greater area for threading to the introducer as compared to a patch body having round edges—such as if the patch were circular or oval shaped. Other patch body configurations are contemplated as should be apparent to one of skill in the art.

The patch body may be formed of a porous material, such as a knit fabric, woven or non-woven fabric, or may be composed of a solid, substantially non-porous, or microporous material. The patch body may be formed of one or more layers of the same or dissimilar material, and the layers may be stacked one on top of the other, side-to-side, or include a combination of both stacking arrangements. The patch body may be formed with portions that are tissue infiltratable and other portions that are less tissue infiltratable or are non-tissue infiltratable, providing selected areas of the repair device with different tissue ingrowth and adhesion resistant properties. The patch body may be formed of permanent material, resorbable material, or a combination of permanent and resorbable materials. It should be appreciated that the patch body may be formed of any biologically compatible material, synthetic or natural, suitable for repairing a tissue or muscle wall defect as would be apparent to one of skill in the art.

A representative embodiment of the hernia repair patch and a representative procedure for using same is now described. A hernia repair patch configured to repair a ventral hernia includes a patch body having a tissue infiltratable layer on one side and a barrier layer on the other side. The tissue infiltratable layer may include one or more sheets of surgical mesh fabric, such as a polypropylene knit. The barrier layer may be a sheet of synthetic or natural barrier material; for example, and without limitation, a sheet of ePTFE may be stitched, heat fused or otherwise connected to a polypropylene sheet. Another option is to embed the polypropylene knit into a film of SEPRA (bioresorbable hydrogel barrier). The polypropylene side would face the abdominal wall and the ePTFE or SEPRA side would face the viscera. A pair of tabs extend outwardly from sides of the patch body. A flat, generally oval-shaped, annular hoisting frame body defines a generally open interior that is intersected by a flat X-shaped pair of force translating arms. At each intersection of the arms and the frame body are enlarged lands that each support a fixating component having an unretracted linear configuration and a retracted coiled configuration. Both the frame body, the X-shaped arms, and the lands are formed of thin NYLON sheet. A tether in the form of a suture extends from the intersection of the arms forming the X-shape; that is, at the approximate center of the force translating arms. Contained within the generally oval frame body is a 0.020 inch diameter nitinol wire that also is generally oval shaped.

The center of the frame body is registered with the center of the patch body, with the frame body generally following the periphery of the patch body. The fixating components are elongated or straightened and passed from the barrier side of the patch body to the tissue infiltratable side, and then allowed to resiliently retract to a coil shape against the tissue infiltratable side, securing the patch body to the hoisting frame. The suture tether is passed through the barrier side and out beyond the tissue infiltratable side where it will be accessible for manipulation to hoist the frame body and associated patch body against the abdominal wall.

The flexible patch and frame are rolled into a small configuration and then delivered through a narrow incision or cannula into a patient. Upon exiting the incision or cannula, the nitinol wire springs back to a larger shape, spreading the patch body into an expanded configuration. The suture tether extending from the patch may be pulled through the abdominal wall, such as by a suture passer, and then manipulated outside of the patient to hoist the frame and assembled patch body against the abdominal wall about the defect. A pulling force on the tether in an outward direction away from the frame and the patch body is directed by the translation component towards the upper and the lower portions of the frame body, helping spread the hoisting force about the frame. With the patch positioned against the abdominal wall, fixation elements, such as a suture, tack, or staple, are applied through the periphery of the patch extending outwardly beyond the frame and, or alternatively, through the openings within the interior of the frame body.

With the patch securely fixated to the abdominal wall, the hoisting frame and self-expanding support member may then be detached from the anchored patch. For example, the surgical team may use a grasper or other laparoscopic instrument to grip and pull the frame away from the patch. In response to the pulling force, the resilient fixating components transform to the unretracted configuration (i.e., linear or substantially linear) allowing the fixating components to slide back through the fixated patch body. Once separated from the patch, the frame and associated self-expanding support member may be withdrawn through the same minimally invasive opening, such as a laparoscopic cannula, via which the assembled hoisting frame and patch were originally delivered to the surgical site.

For purposes of this patent application and any patent issuing thereon, the indefinite articles "a" and "an," as used herein in the specification and in the claims, unless clearly indicated to the contrary, should be understood to mean "at least one." The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. The use of "including," "comprising," "having," "containing," "involving," and/or variations thereof herein, is meant to encompass the items listed thereafter and equivalents thereof as well as additional items.

It should also be understood that, unless clearly indicated to the contrary, in any methods claimed herein that include more than one step or act, the order of the steps or acts of the method is not necessarily limited to the order in which the steps or acts of the method are recited.

Having thus described several aspects of at least one embodiment of this invention, it is to be appreciated various alterations, modifications, and improvements will readily occur to those skilled in the art. Such alterations, modifications, and improvements are intended to be part of this disclosure, and are intended to be within the spirit and scope of the invention. Accordingly, the foregoing description and drawings are by way of example only.

What is claimed is:

1. A prosthesis for repairing a hernia defect, comprising:
    a patch body having a periphery, a first axis and a second axis perpendicular to the first axis, the first axis and the second axis intersecting at approximately a center of the patch body, an upper portion of the patch body on one side of the first axis and a lower portion of the patch body on the other side of the first axis;
    a self-expanding support member to assist in unfurling the patch body from the reduced configuration to an expanded configuration, the self-expanding support member including a first portion that is positionable on the upper portion of the patch body and a second portion that is positionable on a lower portion of the patch body;
    a hoisting frame releasably attachable to the patch body, the hoisting frame defining an open interior and including a translation component extending through the open interior; and
    a tether attached to the translation component, a free end of the tether extendable away from the translation component and through the patch body when the hoisting frame is releasably attached to the patch body, a pulling force on the free end of the tether in an outward direction away from the patch body being directed by the translation component in the direction of a first pair of spaced apart locations on opposite sides of the second axis at the upper portion of the patch body when in the expanded configuration and a second pair of spaced apart locations on opposite sides of the second axis at the lower portion of the patch body;
    wherein the patch body and the hoisting frame when releasably attached to the patch body are manipulable into a reduced configuration for insertion through a narrow incision or cannula into a patient.

2. The hernia repair prosthesis recited in claim 1, wherein the first pair of spaced apart locations coincide with the first portion of the support member and the second pair of spaced apart locations coincide with the second portion of the support member.

3. The hernia repair prosthesis recited in claim 2, wherein an attachment location for releasably attaching the hoisting frame to the patch body is located at or adjacent each of the first pair of spaced apart locations and at or adjacent each of the second pair of spaced apart locations.

4. The hernia repair prosthesis recited in claim 3, wherein a fixating component is located at each attachment location.

5. The hernia repair prosthesis recited in claim 1, wherein the translation component extends between the first portion and the second portion of the self-expanding support member.

6. The hernia repair prosthesis recited in claim 3, wherein the translation component extends between the attachment locations.

7. The hernia repair prosthesis recited in claim 1, wherein the translation component is X-shaped.

8. The hernia repair prosthesis recited in claim 1, wherein the translation component extends at an angle to the second axis of from 20 to 70 degrees.

9. A prosthesis for repairing a hernia defect, comprising:
    a patch body having a periphery, a first axis and a second axis perpendicular to the first axis, the first axis and the second axis intersecting at approximately a center of the patch body, an upper portion of the patch body on one side of the first axis and a lower portion of the patch body on the other side of the first axis;
    a hoisting frame defining an open interior and releasably attachable to the patch body, the hoisting frame including a self-expanding support member to assist in unfurling the patch body from the reduced configuration into an expanded configuration when the frame is releasably attached to the patch body, the hoisting frame having a first axis and a second axis perpendicular to the first axis, the first axis and the second axis intersecting at approximately a center of the hoisting frame, the hoisting frame having an upper portion on one side of the hoisting frame first axis and a lower portion on an opposite side of the hoisting frame first axis, the hoisting frame further including at least two non-self-expanding arms at spaced locations in the open interior on opposite sides of the second axis of the hoisting frame at the both the upper and the lower portions of the hoisting frame, the non-self-expanding arms including a tether attachment portion;
    a tether connected to the tether attachment portion and including a free end that is extendable away from the hoisting frame and through the patch body when the hoisting frame is releasably attached to the patch body, a pulling force on the free end of the tether in an outward direction away from the hoisting frame being directed by the first and second arms to the spaced apart locations on opposite sides of the second axis of the hoisting frame at both the upper and lower portions of the hoisting frame;
    wherein the patch body and the hoisting frame when releasably attached to the patch body are manipulable into a reduced configuration for insertion through a narrow incision or cannula into a patient.

10. The hernia repair prosthesis recited in claim 9, wherein the tether attachment portion is at the approximate center of the hoisting frame.

11. The hernia repair prosthesis recited in claim 9, wherein the self-expanding support member is contained within the hoisting frame.

12. The hernia repair prosthesis recited in claim 9, wherein the non-self-expanding arms intersect at approximately the center of the hoisting frame.

13. The hernia repair prosthesis recited in claim 9, wherein the hoisting frame includes a plurality of attachment locations where the hoisting frame is releasably attachable to the patch body, and the non-self-expanding arms are connected to the plurality of attachment locations.

14. The hernia repair prosthesis recited in claim 9, wherein the non-self-expanding arms extend at an angle to the second axis of from 20 to 75 degrees.

15. A prosthesis for repairing a hernia defect, comprising:
    a patch body having a periphery, a first axis and a second axis perpendicular to the first axis, the first axis and the second axis intersecting at approximately a center of the patch body;
    a hoisting frame releasably attachable to the patch body, the hoisting frame having a frame body defining an open interior and including a first axis and a second axis perpendicular to the first axis, the first axis and the second axis intersecting at approximately a center of the frame body, the center of the frame body being registrable with the center of the patch body when the hoisting frame is releasably attached to the patch body, the frame body including an upper portion on one side of the first axis and a lower portion on an opposite side of the first axis, the hoisting frame further including a first pair of attachment locations at the upper portion and on opposite sides of the second axis for releasably attaching the hoisting frame to the patch body, and a second pair of attachment locations at the lower portion and on opposite sides of the second axis for releasably attaching the hoisting frame to the patch body, the hoisting frame further including a force translation component extending from the first and second pair of attachment locations and through or adjacent the approximate center; and a tether attached to a portion of the force translation component extending through or adjacent the approximate center;

wherein the patch body and the hoisting frame when releasably attached to the patch body are manipulable into a reduced configuration for insertion through a narrow incision or cannula into a patient.

16. The hernia repair prosthesis recited in claim 15, wherein the attachment locations are in the form of lands.

17. The hernia repair prosthesis recited in claim 16, wherein the lands, the frame body, and the force translation component are co-planar.

18. The hernia repair prosthesis recited in claim 15, wherein the frame body includes a self-expanding support member to assist in unfurling the patch body from the reduced configuration into an expanded configuration.

19. The hernia repair prosthesis recited in claim 15, wherein a fixating component is provide at each attachment location.

20. The hernia repair prosthesis recited in claim 18, wherein the attachment locations are at or adjacent the self-expanding support member.

21. The hernia repair prosthesis recited in claim 15, wherein the patch body includes an outermost surface, the hoisting frame being releasably attachable to the outermost surface of the patch body.

22. The hernia repair prosthesis recited in claim 1, wherein the patch body includes an outermost surface, the hoisting frame being releasably attachable to the outermost surface of the patch body.

23. The hernia repair prosthesis recited in claim 9, wherein the patch body includes an outermost surface, the hoisting frame being releasably attachable to the outermost surface of the patch body.

* * * * *